(12) United States Patent
De Jong

(10) Patent No.: US 11,752,449 B2
(45) Date of Patent: Sep. 12, 2023

(54) METHOD OF OPERATING A CRYSTALLIZING VESSEL ASSEMBLY, AS WELL AS A CRYSTALLIZING VESSEL ASSEMBLY

(71) Applicant: IV-CONSULT B.V., Papendrecht (NL)

(72) Inventor: Ricky De Jong, Papendrecht (NL)

(73) Assignee: IV-CONSULT B.V., Papendrecht (NL)

( * ) Notice: Subject to any disclaimer, the term of this patent is extended or adjusted under 35 U.S.C. 154(b) by 0 days.

(21) Appl. No.: 17/779,069

(22) PCT Filed: Nov. 19, 2020

(86) PCT No.: PCT/NL2020/050729
§ 371 (c)(1),
(2) Date: May 23, 2022

(87) PCT Pub. No.: WO2021/101380
PCT Pub. Date: May 27, 2021

(65) Prior Publication Data
US 2023/0001325 A1     Jan. 5, 2023

(30) Foreign Application Priority Data
Nov. 22, 2019  (NL) ..................................... 2024287

(51) Int. Cl.
*B01D 9/00* (2006.01)
*C07C 7/14* (2006.01)

(52) U.S. Cl.
CPC .......... *B01D 9/0013* (2013.01); *B01D 9/0059* (2013.01); *C07C 7/14* (2013.01); *B01D 2009/0086* (2013.01); *C07C 2601/16* (2017.05)

(58) Field of Classification Search
CPC ...... B01D 9/00; B01D 9/0013; B01D 9/0059; B01D 2009/0086; C07C 7/14; C07C 2601/16; B01F 27/15; B01F 27/50; B01F 27/96; B01F 35/92; B01F 2035/98
See application file for complete search history.

(56) References Cited

FOREIGN PATENT DOCUMENTS

| EP | 0916390 A1 | 5/1999 | |
|---|---|---|---|
| JP | 2012246263 A | 12/2012 | |
| WO | WO-2004058377 A1 * | 7/2004 | ........... B01D 9/0004 |

OTHER PUBLICATIONS

International Search report for PCT/NL2020/050729, prepared by the European Patent Office, dated Apr. 9, 2021, 4 pages.

* cited by examiner

*Primary Examiner* — Sharon Pregler
(74) *Attorney, Agent, or Firm* — BROOKS KUSHMAN PC; John E. Nemazi

(57) ABSTRACT

A method of operating a crystallizing vessel assembly, said vessel assembly having a crystallizing vessel, and a rotor comprising a rotor shaft, said rotor including a plurality of rotor arms, said rotor arms having arms attached to the rotor shaft and scrapers attached at the arms. The crystals are grown on the inside of the vessel and the rotor is rotated to scrape said crystals off. To improve liquid flow inside the crystallizing vessel, a plurality of arms of the rotor arms are hollow arms, each arm of the plurality of arms including an inlet opening that is relatively close to the shaft and an outlet opening that is relatively far from the shaft.

10 Claims, 7 Drawing Sheets

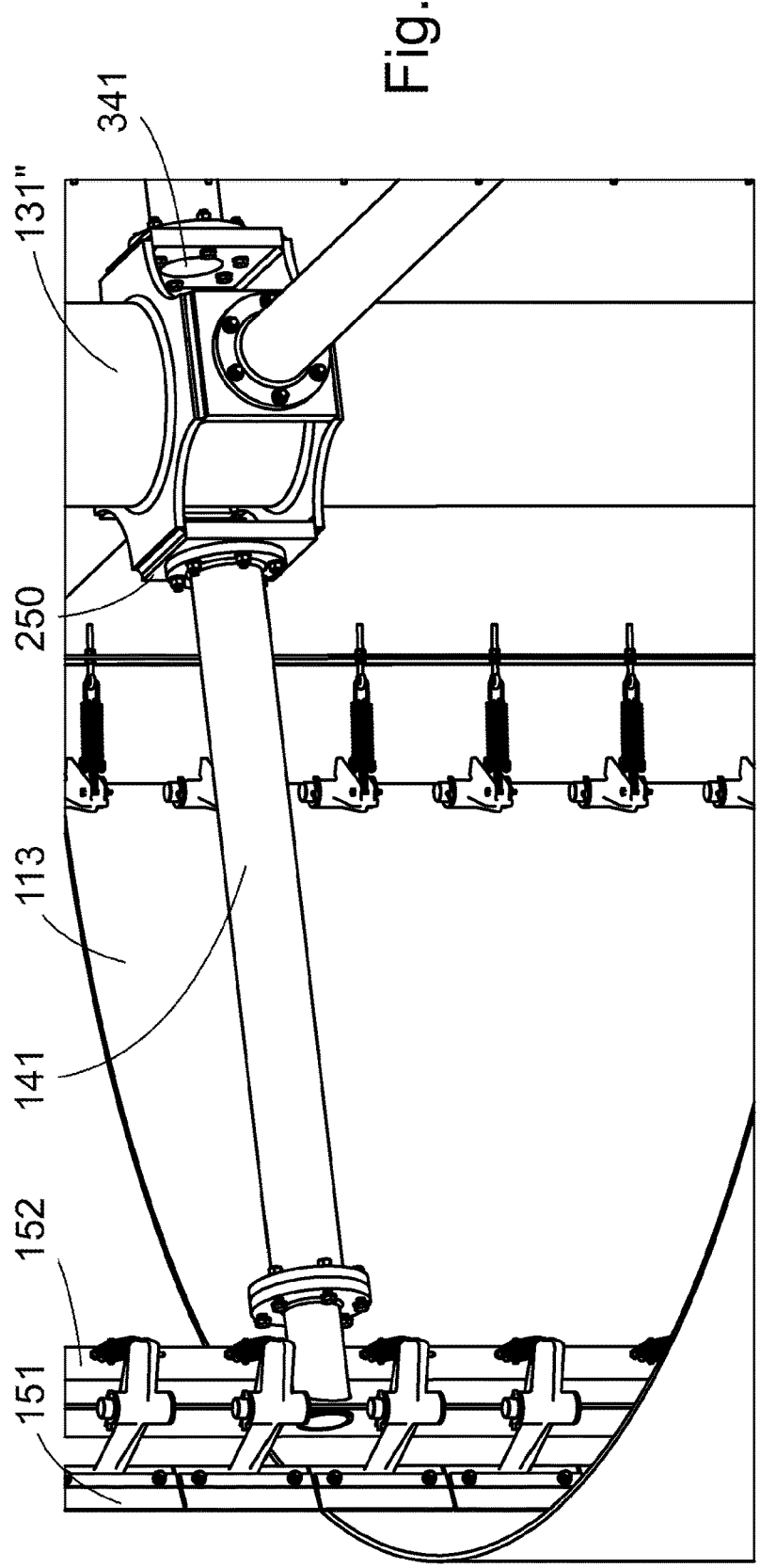

METHOD OF OPERATING A CRYSTALLIZING VESSEL ASSEMBLY, AS WELL AS A CRYSTALLIZING VESSEL ASSEMBLY

CROSS-REFERENCE TO RELATED APPLICATION

This application is the U.S. national phase of PCT Application No. PCT/NL2020/050729 filed on Nov. 19, 2020, which claims priority to NL Patent Application No. 2024287 filed on Nov. 22, 2019, the disclosures of which are incorporated in their entirety by reference herein.

The present invention relates to a method of operating a crystallizing vessel assembly, said vessel assembly comprising
- a crystallizing vessel, said vessel comprising a top wall, a bottom wall and an upright wall extending from the bottom wall to the top wall, said top wall, bottom wall and upright wall defining a lumen,
- a superstructure on top of the vessel, said superstructure comprising a bearing, said bearing comprising an upper race member, a lower race member and roller bodies between said upper race member and said lower race member, said lower race member being attached to the superstructure,
- a rotor, said rotor comprising
    - an upright, rotatable shaft, said shaft comprising i) a top shaft section extending above the top wall and ii) a bottom shaft section in said lumen, said top shaft section being provided with said upper race member, allowing the rotor to rotate along a shaft axis of the upright, rotatable shaft in line with the axis of rotation of the bearing; and
    - a plurality of rotor arms comprising arms attached with proximal ends thereof to said bottom shaft section, and scrapers attached at the distal ends of said arms; wherein crystals are grown on the inside of the upright wall and the rotor is rotated to scrape said crystals off said upright wall.

A method according to the preamble is known in the art. Typically the upright wall of the crystallizing vessel is cooled. An example of a material that is crystallized is para-xylene, a compound used for the production of PET. After discharge from the crystallizing vessel the crystals will be separated from the mother liquor, the latter containing impurities.

In a crystallizing vessel it is important that fresh liquid to be subjected to crystallisation reaches the inner surface of the upright wall.

The object of the present invention is provide a method and a crystallisation vessel for allowing improved liquid flow in the lumen.

To this end, a method according to the preamble is characterized in that a plurality of arms of the rotor arms are hollow arms, each arm of the plurality of arms comprising an inlet opening that is relatively close to the shaft and an outlet opening that is relatively far from the shaft.

It has been found that rotating such an arm in the liquid subjected to crystallisation causes liquid to flow from the centreline of the lumen towards the upright wall. This allows the crystallisation process to be performed quicker (larger through-put) and/or allows for a smaller crystallisation vessel for the same through-put (saving cost).

More specifically, cooling the upright wall results in crystallisation at the surface and a relatively cold solvent that contains a reduced concentration (in moles per litre) of the compound that is crystallized. By transporting liquid from the centreline to the wall, the concentration of the compound near the wall is increased, allowing new crystals to grow at the wall and crystals scraped off from the upright wall to grow.

Typically the crystallisation process will be operated as a continuous process, wherein relatively warm fresh liquid to be subjected to crystallisation is added at one end of the crystallisation vessel (typically the top), and relatively cold liquid (a suspension of crystals in mother liquor) is discharged at the other end.

Typically the inlet and the outlet will be at least 40% of the length of the arm apart, preferably at least 75% of the length of the arm.

The surface area of the inlet opening (or in case the arm has more than one inlet opening the total surface area) is preferably at least 35% of the cross-sectional area of the cross-sectional area (in a direction transverse to the longitudinal direction of the arm) of the lumen of the arm, and preferably at least 70%.

The surface area of the outlet opening (or in case there is more than one outlet opening the total surface area) is preferably at least 35% of the cross-sectional area (in a direction transverse to the longitudinal direction of the arm) of the lumen of the arm, and preferably at least 70%.

According to a favourable embodiment, the arms have a cross-sectional surface area of the lumen in the longitudinal direction of the arm, aid cross-sectional surface having a width/height ratio of at least 1.25, preferably at least 1.5.

This allows the rotor arms to move through the liquid with relative ease, as a result of which in the steady state the arms move faster than the liquid surrounding the arms while liquid inside the arms moves as fast as the arms. As a result, a centrifugal force causes the transport of the liquid to be subjected to crystallisation through the arms.

In practice, at the distal ends of the arms liquid in the vessel is forced to move faster between the arms (fitted with scrapers) and the inner wall of the vessel, causing a zone of reduced pressure, facilitating the flow of liquid inside the arm to flow out.

Relatively flat arms also allow for a reduction in (vertical) mixing, as it is desired to establish a flow from the upright wall towards the rotational axis and in the arm from the rotational axis to the upright wall.

According to a favourable embodiment, the scrapers comprise a scraper profile provided with scraper blades, a scraper profile being attached to the distal ends of at least two arms, said scraper profiles having a tapered cross-section, tapering in the forward direction of the rotating arms.

This allows the rotor arms to move through the liquid with relative ease, as a result of which in the steady state the arms move faster than the liquid surrounding the arms while liquid inside the arms moves as fast as the arms. As a result, a centrifugal force causes the transport of the liquid to be subjected to crystallisation through the arms.

In practice, at the distal ends of the arms liquid in the vessel is forced to move faster between the arms (fitted with scrapers) and the inner wall of the vessel, causing a zone of reduced pressure, facilitating the flow of liquid inside the arm to flow out.

According to a favourable embodiment, para-xylene dissolved in a solvent is introduced into the crystallizing vessel assembly.

The crystallisation of para-xylene is an important application of the method according to the invention. In this particular case the solvent is typically formed by a mixture of isomers, i.e. ortho-xylene and meta-xylene that were also formed during synthesis of para-xylene and (residual) solvent such as benzene and ethylbenzene.

Finally, the present invention relates to a crystallizing vessel assembly, said vessel assembly comprising
- a crystallizing vessel, said vessel comprising a top wall, a bottom wall and an upright wall extending from the bottom wall to the top wall, said top wall, bottom wall and upright wall defining a lumen,
- a superstructure on top of the vessel, said superstructure comprising a bearing, said bearing comprising an upper race member, a lower race member and roller bodies between said upper race member and said lower race member, said lower race member being attached to the superstructure,
- a rotor, said rotor comprising
  - an upright, rotatable shaft, said shaft comprising i) a top shaft section extending above the top wall and ii) a bottom shaft section in said lumen, said top shaft section being provided with said upper race member, allowing the rotor to rotate along a shaft axis of the upright, rotatable shaft in line with the axis of rotation of the bearing; and
  - a plurality of rotor arms comprising
    - arms attached with proximal ends thereof to said bottom shaft section, and
    - scrapers attached at the distal ends of said arms;
wherein a plurality of arms of the rotor arms are hollow arms, each arm of the plurality of arms comprising an inlet opening that is relatively close to the shaft and an outlet opening that is relatively far from the shaft.

This allows the weight of the rotor to be moved from the bearing to the seat in a method according to the present invention.

Typically the inlet and the outlet will be at least 40% of the length of the arm apart, preferably at least 75% of the length of the arm.

The surface area of the inlet opening (or in case there is more than one inlet opening the total surface area) is preferably at least 35% of the cross-sectional area of the cross-sectional area (in a direction transverse to the longitudinal direction of the arm) of the lumen of the arm, and preferably at least 70%.

The surface area of the outlet opening (or in case there is more than one outlet opening the total surface area) is preferably at least 35% of the cross-sectional area of the cross-sectional area (in a direction transverse to the longitudinal direction of the arm) of the lumen of the arm, and preferably at least 70%.

According to a favourable embodiment, the arms have a cross-sectional surface area of the lumen in the longitudinal direction of the arm, aid cross-sectional surface having a width/height ratio of at least 1.25, preferably at least 1.5.

This allows the rotor arms to move through the liquid with relative ease, as a result of which in the steady state the arms move faster than the liquid surrounding the arms while liquid inside the arms moves as fast as the arms. As a result, a centrifugal force causes the transport of the liquid to be subjected to crystallisation through the arms.

In practice, at the distal ends of the arms liquid in the vessel is forced to move faster between the arms (fitted with scrapers) and the inner wall of the vessel, causing a zone of reduced pressure, facilitating the flow of liquid inside the arm to flow out.

According to a favourable embodiment, the scrapers comprise a scraper profile provided with scraper blades, a scraper profile being attached to the distal ends of at least two arms, said scraper profiles having a tapered cross-section, tapering in the forward direction of the rotating arms.

This allows the rotor arms to move through the liquid with relative ease, as a result of which in the steady state the arms move faster than the liquid surrounding the arms while liquid inside the arms moves as fast as the arms. As a result, a centrifugal force causes the transport of the liquid to be subjected to crystallisation through the arms.

In practice, at the distal ends of the arms liquid in the vessel is forced to move faster between the arms (fitted with scrapers) and the inner wall of the vessel, causing a zone of reduced pressure, facilitating the flow of liquid inside the arm to flow out.

According to a favourable embodiment, the plurality of arms is distributed in the longitudinal direction of the axis of rotation on the bottom shaft section.

This allows, in use, the transport of fresh liquid containing a relatively high concentration of compound to be crystallized towards the upright wall over the height of the vessel.

The present invention will now be illustrated with reference to the drawing where FIG. 1A and FIG. 1B show a side view and a cross-sectional view of a crystallizer;

Figure 1A:
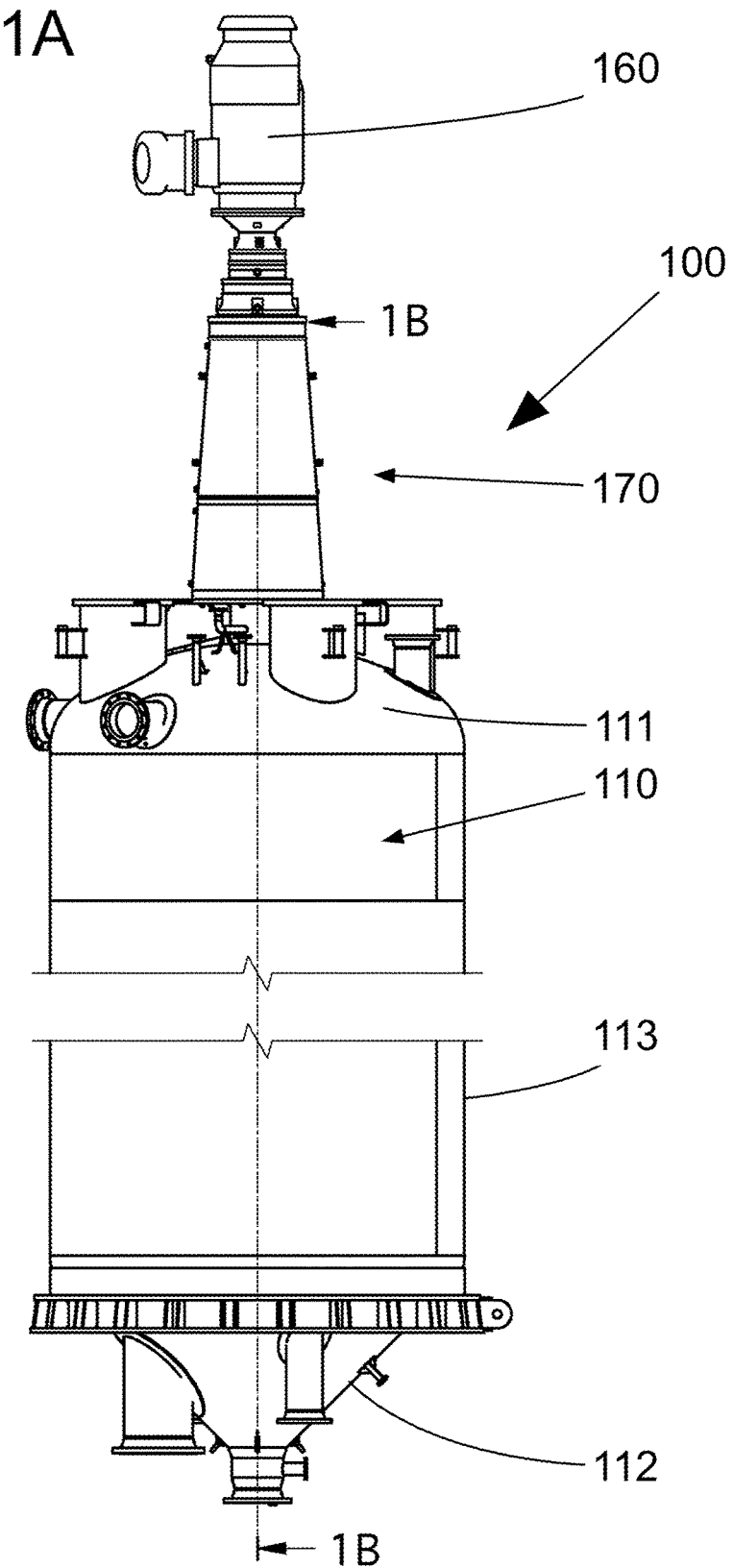
FIG. 1C shows a cross-sectional detail of a superstructure of the crystallizer of FIG. 1B.
Figure 1B:
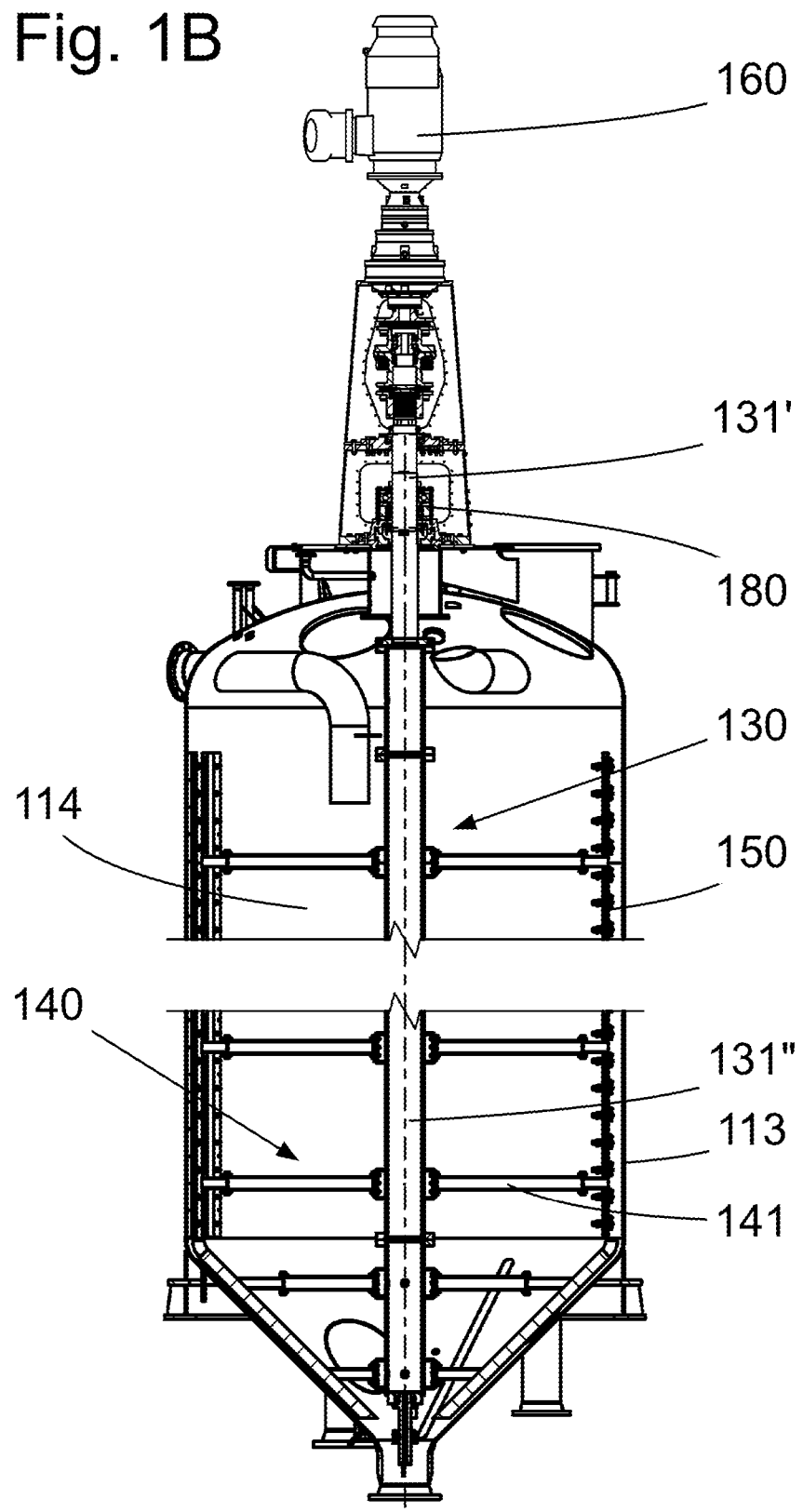

FIG. 1A and FIG. 1B show a side view and a cross-sectional view respectively of a crystallizer vessel assembly 100 comprising a crystallizing vessel 110, said crystallizing vessel 110 comprising a top wall 111, a bottom wall 112 and an upright wall 113 extending from the bottom wall 112 to the top wall 111. The top wall 111, bottom wall 112 and upright wall 113 define a lumen 114 for containing a fluid subjected to crystallisation, such as para-xylene, a compound used for the production of PET.

The crystallizer vessel assembly 100 comprises a rotor 130. The rotor 130 comprises a shaft 131, with a top shaft section 131' extending above the top wall 111 and a bottom shaft section 131" extending in the lumen 114.

The bottom shaft section 131" is provided with a plurality of rotor arms 140. The rotor arms 140 comprise arms 141 provided with scrapers 150. In use, the upright wall 113 will be cooled, causing a component to crystallize against the inside of the upright wall 113. There the crystallized component is scraped from the upright wall 113 and new crystals may form.

On top of the vessel 110 a superstructure 170 (frame) is provided.

Figure 1C:
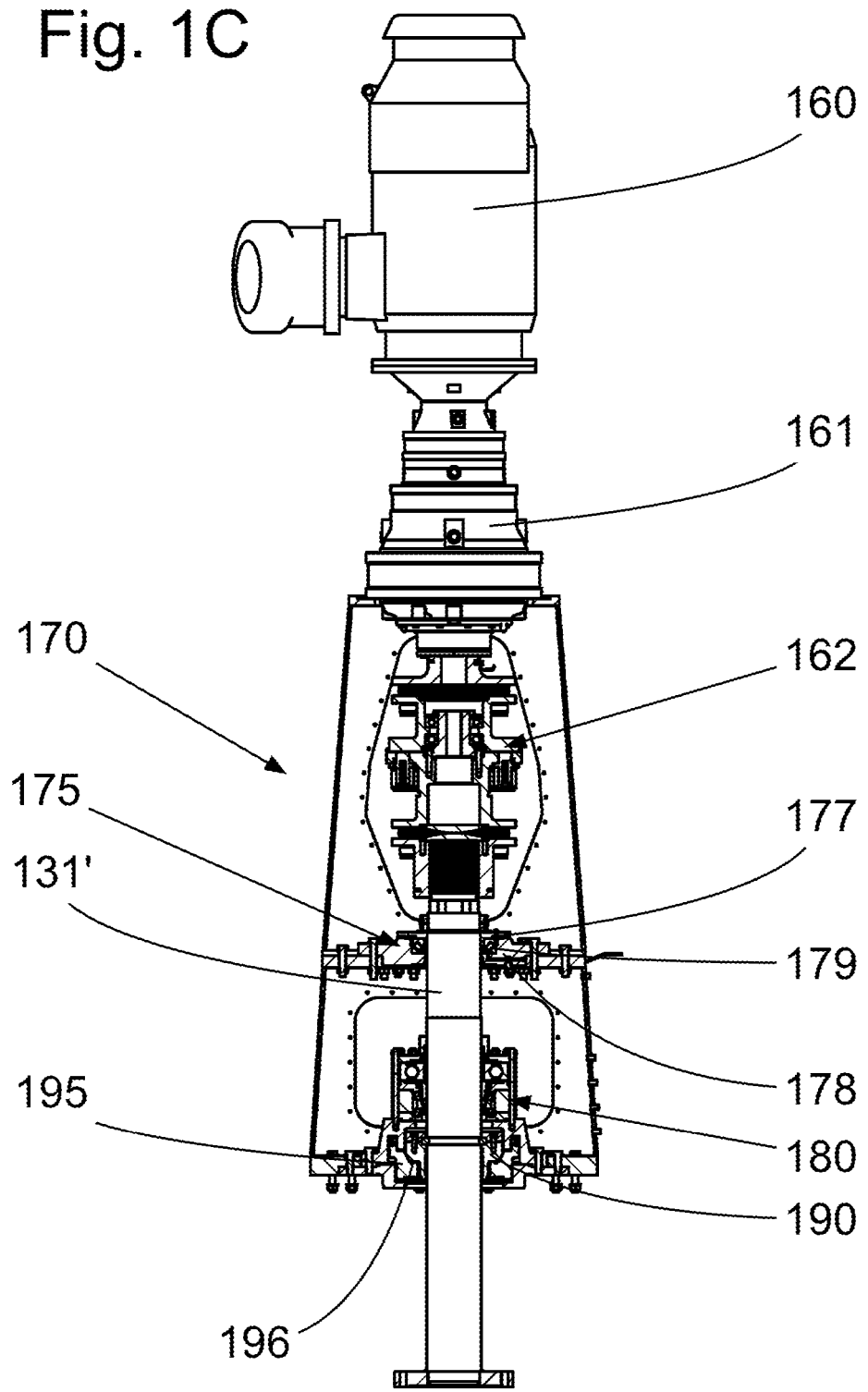

As can be seen in the cross-sectional view of the superstructure FIG. 1C, the superstructure 170 is provided with motor 160 for driving the rotor 130 via a gear box 161 and a torque limiter 162 connected to to the top end of the top shaft section 131'. The torque limiter 162 is provided should the rotor 130 get stuck. A tapered roller bearing 175 is provided to allow the rotor 130 to be suspended from the superstructure 170. A seal 180 is also provided to form a barrier between the lumen 114 and the outside of the vessel 110.

The bearing 175 comprises an upper race member 177 held by the top shaft section 131', a lower race member 178 fixed to the superstructure 170 and tapered roller bodies 179.

Below the seal 180 the top shaft section 131' is provided with a frusto-conically tapered element 190 and the top wall 111 is provided with a seat 195 having a complementary tapered recess 196 for receiving the tapered element 190. When in contact, the contact area of the surface defining the recess 196 and the bottom surface of the frusto-conically tapered element 190 provides for a seal.

Figure 2A:
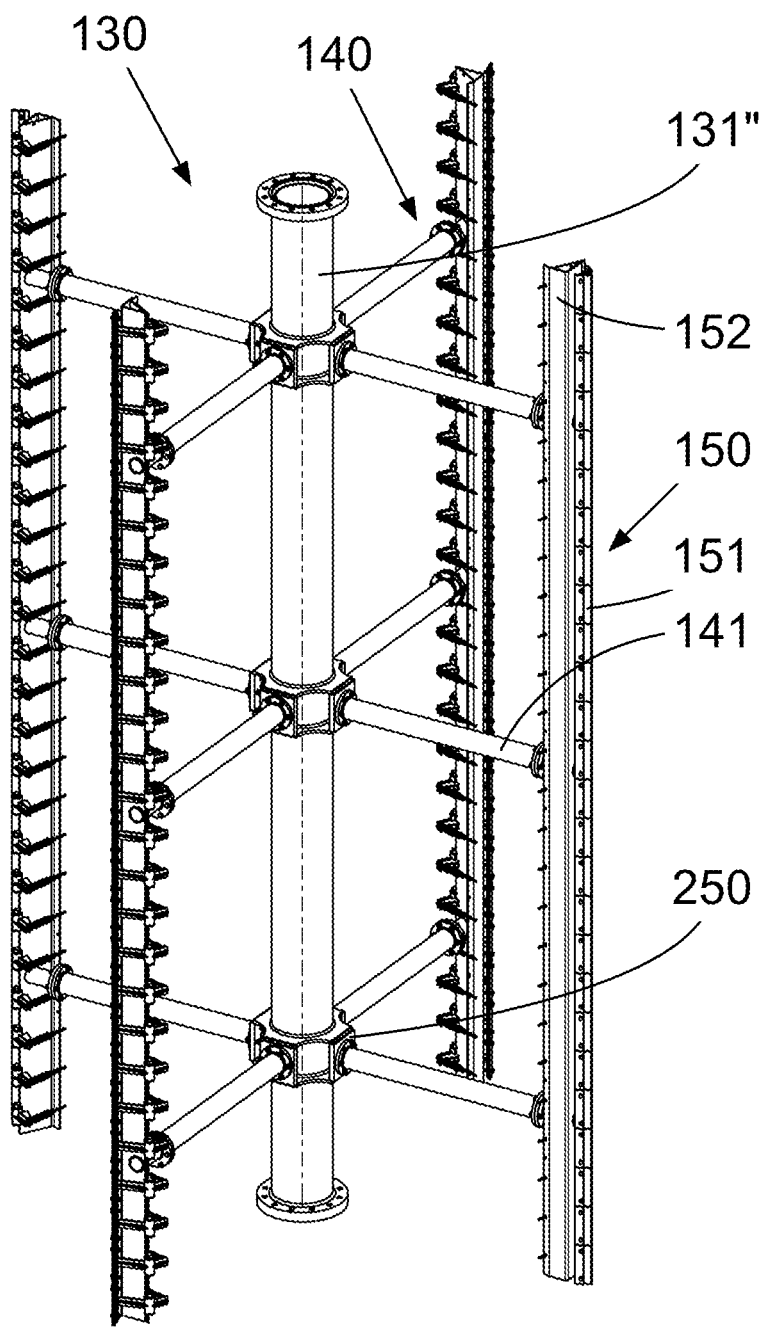
FIG. 2A shows a perspective view of a rotor, with FIG. 2B a cut-out detail view of the rotor inside a crystallizing vessel.

FIG. 2A shows a perspective view of the rotor 130, with FIG. 2B a cut-out detail view of the rotor 130 inside the crystallizing vessel 110 with upright wall 113.

The rotor 130 comprises the bottom shaft section 131" provided with rotor arms 140 comprising scrapers 150. The scrapers 150 comprise a scraper profile 152 provided with scraper blades 151.

In FIG. 2B the scrapers 150 can be seen to extend parallel to the centreline of the rotor and against the inner surface of the upright wall 113. Scrapers are known in the art. The scraper blades 151 scrape crystals from the inner surface of the upright wall 113.

Arms 141 are connected with the proximal ends thereof to fixtures 250, said fixtures 250 being connected to the bottom shaft section 131".

Figure 3A:
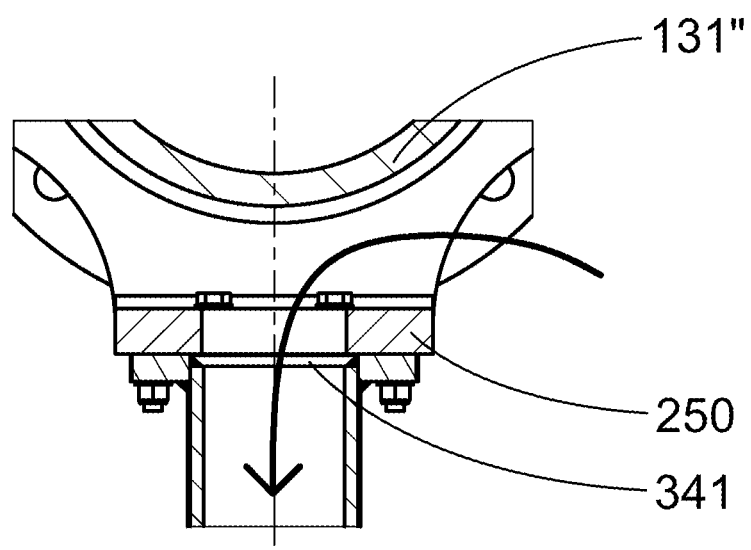
FIG. 3A shows a cross-sectional top view of a rotor shaft provided with a fixture for a rotor arm.

FIG. 3A shows a cross-sectional top view of a rotor shaft 131 provided with a fixture 250 for an arm 141 of a rotor arm 140. The detail drawing shows an inlet opening 341 of the hollow arm 141, an arrow indicating the flow of liquid to be transported towards the upright wall 113.

Figure 3B:
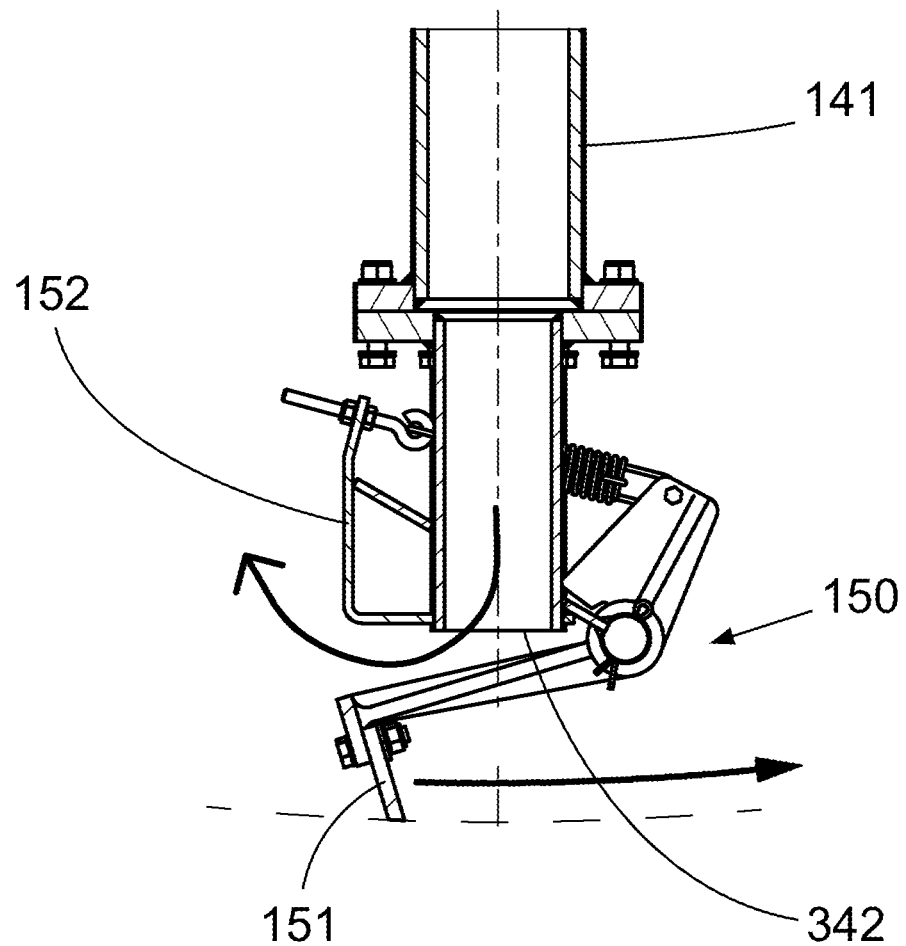
FIG. 3B shows a cross-sectional top view of a distal end of a rotor arm provided with a scraper.

FIG. 3B shows a cross-sectional top view of a distal end of a rotor arm 140. The distal end of the arm 140 is provided with a scraper 150. The arm 140 is hollow and provides an outlet opening 342 arrow indicating the flow of liquid from the hollow arm 140.

Another arrow indicates the rotational direction of the rotor 130.

The invention claimed is:

1. A method of operating a crystallizing vessel assembly, said vessel assembly comprising
a crystallizing vessel, said vessel comprising a top wall, a bottom wall and an upright wall extending from the bottom wall to the top wall, said top wall, bottom wall and upright wall defining a lumen,
a superstructure on top of the vessel, said superstructure comprising a bearing, said bearing comprising an upper race member, a lower race member and roller bodies between said upper race member and said lower race member, said lower race member being attached to the superstructure,
a rotor, said rotor comprising
an upright, rotatable shaft, said shaft comprising i) a top shaft section extending above the top wall and ii) a bottom shaft section in said lumen, said top shaft section being provided with said upper race member, allowing the rotor to rotate along a shaft axis of the upright, rotatable shaft in line with the axis of rotation of the bearing;
and
a plurality of rotor arms comprising
arms attached with proximal ends thereof to said bottom shaft section, and
scrapers attached at the distal ends of said arms;
wherein crystals are grown on the inside of the upright wall and the rotor is rotated to scrape said crystals off said upright wall;
characterised in that a plurality of arms of the rotor arms are hollow arms, each arm of the plurality of arms comprising an inlet opening that is relatively close to the shaft and an outlet opening that is relatively far from the shaft.

2. The method according to claim 1, wherein the arms have a cross-sectional surface area of the lumen in the longitudinal direction of the arm, aid cross-sectional surface having a width/height ratio of at least 1.5.

3. The method according to claim 1, wherein the scrapers comprise a scraper profile provided with scraper blades, a scraper profile being attached to the distal ends of at least two arms, said scraper profiles having a tapered cross-section, tapering in the forward direction of the rotating arms.

4. The method according to claim 1, wherein para-xylene dissolved in a solvent is introduced into the crystallizing vessel assembly.

5. A crystallizing vessel assembly, said vessel assembly comprising
a crystallizing vessel, said vessel comprising a top wall, a bottom wall and an upright wall extending from the bottom wall to the top wall, said top wall, bottom wall and upright wall defining a lumen,
a superstructure on top of the vessel, said superstructure comprising a bearing, said bearing comprising an upper race member, a lower race member and roller bodies between said upper race member and said lower race member, said lower race member being attached to the superstructure,
a rotor, said rotor comprising
an upright, rotatable shaft, said shaft comprising i) a top shaft section extending above the top wall and ii) a bottom shaft section in said lumen, said top shaft section being provided with said upper race member, allowing the rotor to rotate along a shaft axis of the upright, rotatable shaft in line with the axis of rotation of the bearing; and
a plurality of rotor arms comprising
arms attached with proximal ends thereof to said bottom shaft section, and
scrapers attached at the distal ends of said arms;
characterised in that a plurality of arms of the rotor arms are hollow arms, each arm of the plurality of arms comprising an inlet opening that is relatively close to the shaft and an outlet opening that is relatively far from the shaft.

6. The crystallizing vessel assembly according to claim 5, wherein the arms have a cross-sectional surface area of the lumen in the longitudinal direction of the arm, aid cross-sectional surface having a width/height ratio of at least 1.5.

7. The crystallizing vessel assembly according to claim 5, wherein the scrapers comprise a scraper profile provided with scraper blades, a scraper profile being attached to the distal ends of at least two arms, said scraper profiles having a tapered cross-section, tapering in the forward direction of the rotating arms.

8. The crystallizing vessel assembly according to claim 5, wherein the plurality of arms is distributed in the longitudinal direction of the axis of rotation on the bottom shaft section.

9. The method according to claim 1, wherein the arms have a cross-sectional surface area of the lumen in the longitudinal direction of the arm, aid cross-sectional surface having a width/height ratio of at least 1.25.

10. The crystallizing vessel assembly according to claim 5, wherein the arms have a cross-sectional surface area of the lumen in the longitudinal direction of the arm, aid cross-sectional surface having a width/height ratio of at least 1.25.

* * * * *